(12) United States Patent
Kim et al.

(10) Patent No.: US 10,022,477 B2
(45) Date of Patent: Jul. 17, 2018

(54) COMPOSITION FOR ANTI-ADHESION, SURGICAL MESH COMPOSITE WITH ANTI-ADHESION PROPERTY COMPRISING THE SAME AND METHOD FOR PRODUCING THEREOF

(71) Applicant: SAMYANG BIOPHARMACEUTICALS CORPORATION, Seoul (KR)

(72) Inventors: Sun-Woo Kim, Daejeon (KR); Jun-Bae Kim, Daejeon (KR); Guw-Dong Yeo, Daejeon (KR); Hye-Sung Yoon, Daejeon (KR)

(73) Assignee: SAMYANG BIOPHARMACEUTICALS CORPORATION, Seoul (KR)

( * ) Notice: Subject to any disclaimer, the term of this patent is extended or adjusted under 35 U.S.C. 154(b) by 819 days.

(21) Appl. No.: 14/365,924

(22) PCT Filed: Dec. 14, 2012

(86) PCT No.: PCT/KR2012/010925
§ 371 (c)(1),
(2) Date: Oct. 2, 2014

(87) PCT Pub. No.: WO2013/089493
PCT Pub. Date: Jun. 20, 2013

(65) Prior Publication Data
US 2015/0045818 A1  Feb. 12, 2015

(30) Foreign Application Priority Data
Dec. 16, 2011 (KR) .................. 10-2011-0136807

(51) Int. Cl.
*A61B 17/08* (2006.01)
*A61L 31/04* (2006.01)
(Continued)

(52) U.S. Cl.
CPC .......... *A61L 31/041* (2013.01); *A61F 2/0063* (2013.01); *A61L 31/042* (2013.01);
(Continued)

(58) Field of Classification Search
CPC ................. A61F 2/0063; A61F 2/0077; A61F 2002/009; A61F 2002/0091;
(Continued)

(56) References Cited

U.S. PATENT DOCUMENTS 2,265,919 A  12/1941 Lilienfeld et al.
5,569,273 A  10/1996 Titone et al.
(Continued)

FOREIGN PATENT DOCUMENTS

EP         2368523       9/2011
KR    1020020091836    12/2002
(Continued)

OTHER PUBLICATIONS

International Search Report for Application No. PCT/KR2012/010925 dated Apr. 8, 2013 (English Translation, 2 pages).
(Continued)

*Primary Examiner* — Robert Lynch
(74) *Attorney, Agent, or Firm* — Michael Best & Friedrich LLP

(57) ABSTRACT

An anti-adhesion composition with a good anti-adhesion property as well as a good biocompatibility, a surgical mesh composite with anti-adhesion property comprising the same and method for producing the same are provided.

16 Claims, 1 Drawing Sheet

(51) Int. Cl.
*A61F 2/00* (2006.01)
*A61L 31/14* (2006.01)
*B32B 37/06* (2006.01)
*B32B 37/12* (2006.01)
*B32B 37/24* (2006.01)
*A61L 31/06* (2006.01)
*C08L 1/28* (2006.01)

(52) U.S. Cl.
CPC ............ *A61L 31/06* (2013.01); *A61L 31/148* (2013.01); *B32B 37/06* (2013.01); *B32B 37/12* (2013.01); *B32B 37/24* (2013.01); *C08L 1/286* (2013.01); *A61F 2002/009* (2013.01); *A61F 2210/0004* (2013.01); *A61F 2210/0076* (2013.01); *A61F 2240/001* (2013.01); *B32B 2305/38* (2013.01); *B32B 2307/748* (2013.01); *B32B 2309/022* (2013.01); *Y10T 156/10* (2015.01)

(58) Field of Classification Search
CPC . A61F 2240/001; B32B 37/06; B32B 37/065; B32B 2307/748
See application file for complete search history.

(56) References Cited

U.S. PATENT DOCUMENTS

| | | | |
|---|---|---|---|
| 6,045,571 A | 4/2000 | Hill et al. | |
| 6,287,316 B1 | 9/2001 | Agarwal et al. | |
| 7,514,097 B1* | 4/2009 | Himeda | A61L 15/28 424/444 |
| 2003/0100955 A1 | 5/2003 | Greenawalt et al. | |
| 2003/0124087 A1 | 7/2003 | Kim et al. | |
| 2004/0175354 A1* | 9/2004 | Gradl | G01N 33/54393 424/78.38 |
| 2007/0219568 A1 | 9/2007 | Yeo et al. | |
| 2009/0275979 A1 | 11/2009 | Im et al. | |
| 2012/0082712 A1* | 4/2012 | Stopek | A61L 17/005 424/423 |
| 2014/0112972 A1* | 4/2014 | Noishiki | A61L 31/042 424/444 |

FOREIGN PATENT DOCUMENTS

| | | |
|---|---|---|
| KR | 1020030055102 | 7/2003 |
| KR | 100673596 | 1/2007 |
| KR | 100729415 | 6/2007 |
| KR | 1020080058043 | 6/2008 |
| KR | 20080062254 | 7/2008 |
| KR | 1020100073443 | 7/2010 |
| WO | 2001087365 | 11/2001 |

OTHER PUBLICATIONS

Extended European Search Report from the European Patent Office for Application No. 12858038.8 dated Jul. 13, 2015 (10 pages).

Greenawalt et al., "Evaluation of Sepramesh Biosurgical Composite in a Rabbit Hernia Repair Model", Journal of Surgical Research, Academic Press Inc., San Diego, CA, US, vol. 94, Dec. 1, 2000, pp. 92-98.

Noishiki et al., "Anti-adhesive Membrane for Pleural Cavity", Artificial Organs, Blackwell Scientific Publications Inc., Boston, US, vol. 34, No. 3, Mar. 1, 2010, pp. 224-229.

* cited by examiner

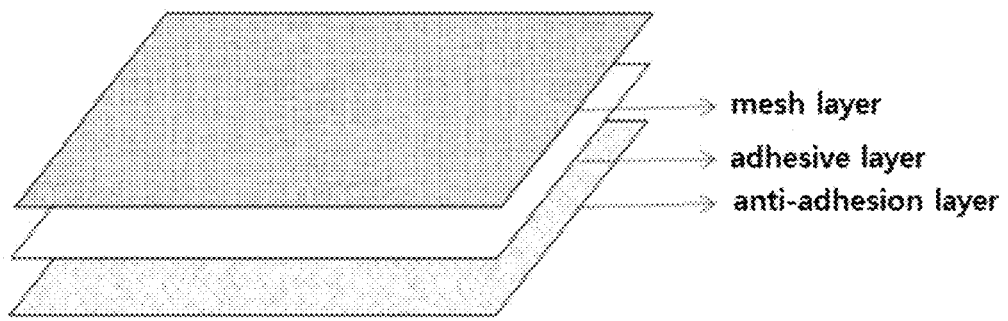

COMPOSITION FOR ANTI-ADHESION, SURGICAL MESH COMPOSITE WITH ANTI-ADHESION PROPERTY COMPRISING THE SAME AND METHOD FOR PRODUCING THEREOF

TECHNICAL FIELD

The present invention provides an anti-adhesion composition with a good anti-adhesion property as well as a good biocompatibility, a surgical mesh composite with anti-adhesion property comprising the same and method for producing the same.

BACKGROUND

Generally, a tension-free repair of surgery has been widely used for the hernia repair, because it has a low relapse rate and a short operation time, and a short wound recovery time for the patient to return to daily life. The mesh used for hernia repair must maintain chemical and physical properties in several years to strengthen the peritoneum, and thus filaments prepared from unabsorbable polymer such as polypropylene, polyethyleneterephthalate, and the like have been widely used as its material.

As fibrous tissues are excessively generated or bloods are run out and coagulated in the recovery course of wounds in inflammation, gash, friction, surgery cuts, etc., the surrounding organs or tissues being separated from each other adhere together, and so adhesion occurs. The wound caused by surgery adheres to the other tissue adjacent to surgical region to induce pain, intestinal obstruction, adhesion and the like. Occasionally, the re-surgery needs to separate the adhered part.

As the methods for preventing the adhesion, the anti-adhesion agent in solution, gel, film and the like is inserted during the surgery. The material useful for the anti-adhesion agent can be a material functioning as a barrier during the wound healing and then being degraded, has no toxicity, and does not produce the toxic degraded products. The examples of materials used for the anti-adhesion agent include expanded poly tetrafluoroethylene (ePTFE), poly vinyl alcohol (PVA) and etc. as a unabsorbable material; and the natural polymers derived from a living body such as polysaccharides and proteins, and the un-natural polymers, soluble synthetic polymer and the like. The materials for anti-adhesion agent can be used alone, or in combination with other polymers in the chemically-bound form, film, or sheet.

The mesh composite products having an anti-adhesion property and the mesh basic function have been developed as the surgical mesh for heniotomy. Among the mesh composite products, there is a knitted mesh of polypropylene monofilament which are adhered by oxidized regenerated cellulose (ORC), unabsorbable material of silicone elastomer or ePTFE. The fabric prepared by ORC has been known to have a good adhesion to the winding organ or tissue, but has no biocompatibility due to an artificial polymer and a low efficiency of separating membrane, because it can be easily penetrated by cell, blood protein and the like through the large pore. The unabsorbable materials such as ePTFE cannot be degraded biologically, and has a disadvantage of induction of inflammation in the surgical regions.

In addition, there is another type of mesh composite which is prepared by making the knitted fabric of unabsorbable material such as polypropylene and combining it with hydrogel such as hyaluronic acid or CMC hydrogel with an adhesive. The toxic cross-linking agent must be used for preparing the insoluble anti-adhesion layer with hyaluronic acid and CMC, but be removed by complex purification steps. Two-layered mesh composite of polyester/collagen film has been provided. The collagen can cause the immune-rejection and provide animal pathogens and viruses, because it is derived from animal. Other two-layered mesh composite is prepared by performing the electrical spinning for heparin to obtain a heparin web and for PLGA copolymer on the heparin web. The remaining amount of organic solvent required for the electrical spinning cannot be controlled easily and the web has a low physical strength and productivity.

The mesh composite used for the hernia repair surgery needs high surgical convenience, alleviation of the patient's irritation feeling, and biocompatibility. Because the mesh composite has a multi-layered structure largely, it requires flexibility. The unabsorbable polymer used for anti-adhesion agent can be a cause of re-adhesion as time goes on, and the absorbable polymer can induce the inflammation in the absorption process. Accordingly, there is a need for developing mesh composite that can satisfy the requirements of the surgical mesh composite and resolve the problems of the products in related art.

SUMMARY OF THE INVENTION

In order to solve the aforementioned problems and comply with the requirements, it is an object of the present invention to provide a composition for anti-adhesion having surgical convenience, a reduced feeling of irritation of patient, and increased anti-adhesion property after surgery with maintaining the good biocompatibility, flexibility, strength and lightness of mesh.

The present invention is to provide a surgical mesh composite with the anti-adhesion property and a preparation method of the same.

BRIEF DESCRIPTION OF THE DRAWINGS

FIG. 1 shows a schematic drawing of the three-layered mesh composite including a surgical mesh layer and an anti-adhesion layer mediated by a biodegradable polymer adhesive layer in accordance with an embodiment of the present invention.

DETAILED DESCRIPTION

To resolve the problems of the related art, the present inventors have performed continuous studies. As a result, the inventors found that the modification of carboxymethylcellulose (CMC) with a specific viscosity to be insoluble increases the anti-adhesion property, and that the surgical convenience and the patient's feeling of irritation are reduced and the biocompatibility and flexibility are increased by providing the surgical mesh composite including further an anti-adhesion layer made of the modified CMC to a surgical mesh layer, and that the anti-adhesion after surgical operation is notably improved with maintaining the flexibility, strength and lightness of mesh, to complete the present invention.

An embodiment of the present invention provides an anti-adhesion agent including an insoluble carboxymethylcellulose layer where the insoluble carboxymethylcellulose is obtained by performing a heat treatment of a carboxymethylcellulose having 100 cps to 500 cps of viscosity in 1 wt % of an aqueous solution under vacuum.

Another embodiment provides a surgical mesh composite including a surgical mesh layer and an anti-adhesion layer and having an anti-adhesion property, where the anti-adhesion layer comprises an insoluble carboxymethylcellulose formed by performing heat treatment at a vacuum atmosphere for a carboxymethylcellulose having a viscosity of 100 cps to 500 cps in 1 wt % of aqueous solution, Further embodiment provides a method of producing a surgical mesh composite with an anti-adhesion property, including the steps of providing a surgical mesh layer;

preparing an anti-adhesion layer comprising an insoluble carboxymethylcellulose which is formed by heat treatment of carboxymethylcellulose with a viscosity of 100 cps to 500 cps in 1 wt % of aqueous solution under vacuum; and adhering the anti-adhesion layer on the surgical mesh layer.

Herein, the term "surgical mesh composite" means a multilayered structure including a surgical mesh layer and an anti-adhesion layer which are attached each other.

Herein, the term "carboxymethylcellulose" means a cellulose backbone formed by a glucopyranose monomer having hydroxyl group of which the part is bonded by carboxymethyl group ($-CH_2-COOH$). It is usually used as an alkali metal salts, such as sodium salt, and thus the term includes the carboxymethylcellulose and its alkali metal salts.

The anti-adhesion agent of the present invention, the components of the surgical mesh composite, and the preparation method thereof will be described in more detail hereinafter.

<Anti-Adhesion Agent/Anti-Adhesion Layer>

Adhesion occurs, when the surrounding organs or tissues which are supposed to be separated from each other adhere together where fibrous tissues are excessively generated or bloods are run out and coagulated in the recovery course of wounds in inflammation, gash, friction, surgery cuts, etc.

To prevent the adhesion, in accordance with the present embodiment, an anti-adhesion agent including the insoluble carboxymethylcellulose layer is provided. A surgical mesh composite including a surgical mesh layer and an anti-adhesion layer comprised of the anti-adhesion agent is provided.

The surgical mesh composite includes an anti-adhesion layer which is formed by the anti-adhesion agent including insoluble carboxymethylcellulose. The following descriptions for the anti-adhesion agent are also applicable to the surgical mesh composite.

The anti-adhesion agent includes the insoluble carboxymethylcellulose alone, or in combination with a hydroxyl group-containing compound. Preferably, the anti-adhesion agent includes a mixture of the insoluble carboxymethylcellulose and the hydroxyl group-containing compound.

The hydroxyl group-containing compound can be contained at an amount of 100 parts by weight or less, for example 10 to 80 parts by weight, or more preferably 20 to 50 parts by weight with respect to 100 parts by weight of carboxymethylcellulose. When the amount of hydroxyl group-containing compound exceeds the ranges, the color change of final insoluble carboxymethylcellulose layer and the reduced adhesion to the mesh layer can occur. When the amount of hydroxyl group-containing compound is less than the ranges, the sufficient anti-adhesion property cannot be obtained due to the reduced insolubility.

The carboxymethylcellulose is one of the biodegradable polymers, because the carboxyl group is capable of reacting with the hydroxyl group to form an ester bond.

The content of sodium (Na) in the carboxymethylcellulose ranges 4 to 10%, or more preferably 6.5 to 8.5%. When the sodium content is less than the ranges, the carboxymethylcellulose cannot be dissolved or requires a long time for being dissolved in water due to the low water-solubility. When the sodium content is higher than the ranges, the increased probability of reaction of carboxymethylcellulose with the hydroxyl group cause the heat-treated insoluble carboxymethylcellulose to remain in the body for a long time, thereby decreasing the anti-adhesion property.

The viscosity of carboxymethylcellulose ranges 100 cps to 500 cps, or more preferably 200 to 400 cps at 1 wt % aqueous solution. When the solution viscosity is lower than the ranges, the short retention time of the insoluble carboxymethylcellulose after being insoluble by performing the heat treatment reduces the anti-adhesion efficiency. When the solution viscosity is higher than the ranges, excessive long retention time of insoluble carboxymethylcellulos causes the body reaction to foreign material, thereby decreasing the anti-adhesion efficiency.

The hydroxyl group-containing compounds include, for example, a polyhydric alcohol or a multi-arm polyethylene glycol having a multifunctional group. The multi-arm polyethylene glycol includes the low number of terminal functional groups, and preferably, the PEG having a low molecular weight of 1,000 or lower, in order to increase the formation of covalent ester bond.

The polyhydric alcohol can be any biocompatible alcohol including at least 2 hydroxyl groups in a molecule, for example, sorbitol, glycerol, etc., but not limited thereto.

The anti-adhesion layer can be contained at an amount of 10 to 90 parts by weight, preferably 10 to 50 parts by weight, or more preferably 20 to 30 parts by weight with respect to 100 parts by weight of the surgical mesh composite. When the amount of anti-adhesion layer is less than the ranges, the anti-adhesion effect can hardly be obtained. When the amount is higher than the ranges, the mesh composite can hardly be positioned at a surgical region accurately due to the low flexibility of the mesh composite, and the feeling of irritation can be continuously after surgery due to the swelling of insoluble carboxymethylcellulose in the anti-adhesion layer, until the insoluble carboxymethylcellulose is absorbed.

Preferably, the anti-adhesion layer in the form of sponge or foam can be prepared by dissolving carboxymethylcellulose in water to make carboxymethylcellulose solution, freezing the carboxymethylcellulose solution alone or with the addition of the hydroxyl group-containing compound, and drying, preferably under vacuum.

The carboxymethylcellulose can be a water-insoluble modified type preferably. The water-insoluble modified type can be obtained by freezing the carboxymethylcellulose solution alone or with the addition of the hydroxyl group-containing compound, and then by treating the dried product at a high temperature and vacuum atmosphere.

The heat treatment can be carried out under the reduced pressure of 2000 mmHg or lower, for example 1 to 2,000 mmHg, or preferably 1,000 mmHg or lower, for example 1 to 1,000 mmHg, and at a high temperature of 100 to 160° C., or preferably 120 to 140° C., to produce insoluble carboxymethylcellulose.

The heat treatment can be carried out for 6 to 24 hours, or preferably 12 to 18 hours. The time and temperature of the heat treatment are related with the retention time of the insoluble carboxymethylcellulose inside body. When the time and the temperature do not reach the ranges, the anti-adhesion efficiency may be lowered due to the short retention time of the insoluble carboxymethylcellulose. On the other hand, when the time and the temperature exceed the ranges, the irritation reaction occurs and the anti-adhesion efficiency may be reduced due to the long retention time.

In the case that the anti-adhesion layer includes a mixture of the insoluble carboxymethylcellulose and the hydroxyl group-containing compound, the mixture of the insoluble carboxymethylcellulose and hydroxyl group-containing compound can be prepared by 1) dissolving an alkali salt of carboxymethylcellulose, preferably sodium salt of carboxymethylcellulose, in water and then adding the hydroxyl group-containing compound, to obtain the mixed aqueous solution; 2) freezing and drying the mixed aqueous solution under vacuum to produce the mixture of the alkali salt of carboxymethylcellulose and the hydroxyl group-containing compound; and 3) performing the heat treatment of the mixture at a pressure of 10 to 2,000 mmHg, or preferably 1,000 mmHg or lower and at a temperature of 100 to 150° C., or preferably 120 to 160° C.

In the step 1), preferably, the alkali salt of carboxymethylcellulose, preferably sodium salt of carboxymethylcellulose can be dissolved at a concentration of 0.1 wt % to 2 wt %.

The hydroxyl group-containing compound can be preferably a polyhydric alcohol and can be used at an amount of 100 parts by weight or lower, for examples 10 to 80 parts by weight, or more preferably 20 to 50 parts by weight, with respect to 100 parts by weight of sodium salt of carboxymethylcellulose.

<Surgical Mesh Layer>

A surgical mesh used for the surgical mesh layer is not limited specially and can be any kinds of surgical mesh which are generally used for surgery. The examples of surgical meshes are disclosed in the present inventor's related arts such as KR 10-0673596B, KR10-0729415B, KR10-0946338B and KR10-0970738B.

In general, the surgical mesh has a porous mesh structure such as knitted fabric of circular knitted fabric or warp knit and has a sufficient flexibility used for surgery, a physical strength endured in the pressure inside body. The surgical mesh can provide a good adhesion property to the tissue or organ due to the good cell growth on the mesh structure.

In an embodiment, the surgical mesh can be at least one selected from the group consisting of:

i) a mesh including a mono- or multi-filament of unabsorbable polymer, ii) a mesh including monofilament prepared by conjugate spinning of unabsorbable polymer and absorbable polymer, and iii) a mesh prepared by mixed spinning of mono- or multi-filaments of unabsorbable polymer and absorbable polymer.

The unabsorbable polymer can be preferably at least one polymer selected from the group consisting of polyolefins such as polypropylene, polyethylene and a copolymer of ethylene and propylene; thermoplastic saturated polyesters; polyamides such as nylon 6, nylon 66 and the like; polyurethanes; polyvinylidenes; and fluoropolymers, and more preferably can be polyolefins, thermoplastic saturated polyesters or a mixture thereof.

The absorbable polymer can be preferably at least a homopolymer prepared from a monomer selected from the group consisting of glycolide, glycolic acid, lactide, lactic acid, ε-caprolactone, ρ-dioxanone, trimethylene carbonate, polyanhydride and polyhydroxyalkanoate, or a copolymer prepared from at least 2 monomers selected from the group consisting of glycolide, glycolic acid, lactide, lactic acid, ε-caprolactone, ρ-dioxanone, trimethylene carbonate, polyanhydride and polyhydroxyalkanoate. More preferably, the absorbable polymer can be at least a homopolymer prepared from a monomer selected from the group consisting of glycolide, glycolic acid, lactide, lactic acid, ε-caprolactone, or a copolymer prepared from at least 2 monomers.

Preferably, the surgical mesh can be ii) a mesh including a monofilament prepared by conjugate spinning of unabsorbable polymer and absorbable polymer. The monofilaments prepared by conjugate spinning can be divided to sea/islands type, segmented-pie type, side-by-side type or sheath/core type in the cross-sectional structure, and preferably has the segmented-pie type.

In case of the segmented-pie type monofilament, the adhesion of the mesh to the tissue can be improved with obtaining the peritoneum fluidity, because the absorbable material and the unabsorbable material of the mesh are positioned uniformly on the surface of fabric so the fat tissue formed around the absorbable material and the connective tissue formed around the unabsorbable material are suitably combined. Unlike the sea/islands type and sheath/core type of unabsorbable material surrounded by absorbable material, the segmented-pie type monofilament binds to the tissue and induces the strong adhesion with the tissue at an initial stage.

In accordance with an embodiment of the present invention, the segmented-pie type monofilament used for the surgical mesh includes unabsorbable polymer and absorbable polymer conjugate spun in a longitudinal direction, and has a cross-section of segmented-pie type where the unabsorbable polymer and the absorbable polymer are positioned alternatively. Preferably, the unabsorbable polymer is separate each other by absorbable polymer and the absorbable polymer is continuously connected. The segmented-pie type monofilament can include 3 to 10 segments, or preferably 3 to 6 segments.

The segmented-pie type monofilament is in a monofilament before initial degradation, but unabsorbable polymers are divided into strands like the multi-filament to show the flexibility, when the absorbable polymer degrades in a certain time. Compared to the conventional mesh including unabsorbable material alone and other sea/islands type mesh, the segmented-pie type monofilament can provide the mesh having the biocompatibility and the flexibility with reducing the initial amount and retained amount of the material.

The method of preparing the segmented-pie typed monofilament using conjugate spinning is not limited particularly, and can adopt any method known in the art. For example, the segmented-pie typed monofilament can be prepared by melting the polymers using two extruders respectively, discharging a desired amount of each melted polymer through the quantitative pump to control the mixing ratio of each polymer, and performing conjugate spinning the discharged melting polymer through the conjugate spinning block to produce each conjugate spun strand.

The amount of the absorbable polymer can be 30 to 70 vol % and the amount of unabsorbable polymer can be 30 to 70 vol %. When the amount of absorbable polymer is less than 30 vol %, the unabsorbable polymer cannot be separated and thus obtained in a continuous form in the spinning process due to low volume of absorbable polymer. On the other hand, when the amount of unabsorbable polymer is less than 30 vol %, the minimum strength of fiber cannot be maintained due to the low amount of the retained unabsorbable material after degradation, the sea/islands type fiber can be prepared in the form of unabsorbable polymer surrounded with the absorbable polymer. More preferably, the amount of absorbable polymer can be 40 to 60 vol %, and the amount of unabsorbable polymer can be 40 to 60 vol %.

In order that the kind and the size of mesh can be easily distinguished in the surgery, the mesh including the dyed fiber at an interval can be used. The absorbable polymer is dyed only for preventing the remaining of dye inside body. The dye cannot be limited particularly, and for example can be dyes used widely for a surgical suture, such as D&C violet No. 2, D&C Green No. 6, FD&C Blue No. 2 and the like.

The mesh can be a fabric with various structures and shapes, such as rectangular, hexagonal or net shapes, and the mesh density can be preferably 20 gauges/inch with respect to the needle interval of warp knitting machine.

The mesh can have a pore size of 0.1 to 4.0 mm, or preferably 0.2 to 3.0 mm.

The thickness of mesh composite can be preferably 100 to 900 μm, or more preferably 500 to 700 μm. When the thickness of mesh composite is lower than 100 μm, the mesh cannot have a sufficient strength which is capable of enduring the intra-abdominal pressure. When the thickness is higher than 900 μmm, intra-abdominal feeling of irritation increases.

<Biodegradable Polymer Adhesive Layer>

In accordance with an embodiment, a surgical mesh composite having an anti-adhesion property includes further a biodegradable polymer adhesive layer positioned between the surgical mesh layer and the anti-adhesion layer including the insoluble carboxymethylcellulose.

The surgical mesh layer and the anti-adhesion layer including the insoluble carboxymethylcellulose can be adhered strongly due to the biodegradable polymer adhesive layer. Because the adhesions between the layers are maintained for a long time after being applied to the body, the anti-adhesion property can be increased.

The surgical mesh composite includes preferably a surgical mesh layer; a biodegradable polymer adhesive layer; and an anti-adhesion layer including an insoluble carboxymethylcellulose which are stacked sequentially and adhered.

The biodegradable polymer adhesive layer is in a sheet, a film, a sponge, foam and the like, and can be prepared by solvent casting method, electrical spinning, film molding process, and the like.

The biodegradable polymer is a homopolymer or a copolymer prepared from at least a monomer selected from the group consisting of glycolide, glycolic acid, lactide, lactic acid, ε-caprolactone, ρ-dioxanone, trimethylene carbonate, polyanhydride and polyhydroxyalkanoate, and has a weight-average molecular weight of preferably 10,000 to 200,000 Da, or more preferably 50,000 to 150,000 Da.

Preferably, the biodegradable polymer can be copolymer of glycolic acid and lactide, for example at a mixing weight ratio of 1:9 to 9:1, or preferably 2:8 to 8:2.

In addition, the biodegradable adhesive polymer layer has a thickness of 0.1 to 20%, with respect to the total thickness of surgical mesh composite.

Preferably, the biodegradable adhesive polymer layer can be contained at an amount of 0.1 to 60 parts by weight, with respect to 100 parts by weight of surgical mesh composite.

The surgical mesh composite can be prepared by adhering the surgical mesh layer and the anti-adhesion layer, and for example, the adhering can be performed by positioning and heat-sealing an adhesive layer between the surgical mesh layer and the anti-adhesion layer.

The heat-sealing process can be carried out with the thermo-compression method, and for example, by adhering the layers on the hot plate heated to 50 to 200° C. or preferably 90 to 160° C. under a pressure of 10 to 1500 psi or preferably 20 to 1000 psi. when the temperature of hot plate is lower than 50° C., the mesh composite dose not adhere to the mesh due to the reduced flexibility. When the temperature of hot plate is higher than 200° C., it can produce stiff mesh composite or cause the basic structure of mesh to be impaired. Preferably, the time of heat-sealing can be 2 to 300 seconds, or more preferably 10 to 120 seconds.

After the surgical mesh composite prevents the adhesion caused by surgery such as hernia repair surgery, the polymer with anti-adhesion property is absorbed into the body fast and excreted out, and the mesh layer is continuously maintained to prevent the recurrence of hernia.

The mesh composite has a good flexibility, lightness, and dimensional stability, and thus it can be easily handled during surgery, alleviate the irritation feeling of patient, and have a sufficient physical strength for enduring the intra-abdominal pressure. Most of all, the mesh composite of the present invention can increase the anti-adhesion effect remarkably after surgery.

EXAMPLES

Hereinafter, the present invention is described further through examples. However, the following examples are only given for the understanding of the present invention and the present invention is not limited to or by them.

Examples 1 to 11 and Comparative Examples 1 to 4

Preparation of Anti-Adhesion Layer Including an Insoluble Sodium Carboxymethylcellulose As disclosed in Table 1, the dried carboxymethylcellulose-Na salt (Bolak) was added to 500 ml beaker, added with 5000 ml of distilled water and dissolved with a mechanical stirrer at 300 rpm for 6 hours. To the aqueous solution was added glycerol at an amount of glycerol in Table 1 or not, and then stirred with a magnetic rotary stirrer for 2 hours, to obtain a mixed aqueous solution of carboxymethylcellulose-Na salt and glycerol or an aqueous solution of carboxymethylcellulose-Na salt. Then, a part of the mixed aqueous solution was taken and poured to a petri dish, and frozen at a freezer for 24 hours. The frozen mixed solution of carboxymethylcellulose-Na salt and glycerol was dried for 12 hours under vacuum to produce a mixed product of carboxymethylcellulose-Na salt and glycerol in a sponge form. The mixed product was performed with heat treatment at a temperature of Table 1, to produce final mixed product of the insoluble carboxymethylcellulose and glycerol or final product of the insoluble carboxymethylcellulose.

TABLE 1

The condition of preparation for the insoluble carboxymethylcellulose

| Number of Examples | carboxymethylcellulose-Na salt with viscosity of 1% solution (cps) | Temperature of heat treatment (° C.) | Content of glycerol$^a$ (wt %) |
|---|---|---|---|
| Example 1 | 110 | 130 | 30 |
| Example 2 | 200 | 130 | 30 |
| Example 3 | 300 | 130 | 0 |

TABLE 1-continued

The condition of preparation for the insoluble carboxymethylcellulose

| Number of Examples | carboxymethylcellulose-Na salt with viscosity of 1% solution (cps) | Temperature of heat treatment (° C.) | Content of glycerol[a] (wt %) |
|---|---|---|---|
| Example 4 | 300 | 130 | 10 |
| Example 5 | 300 | 130 | 30 |
| Example 6 | 300 | 130 | 50 |
| Example 7 | 450 | 130 | 10 |
| Example 8 | 300 | 100 | 20 |
| Example 9 | 300 | 120 | 20 |
| Example 10 | 300 | 140 | 20 |
| Example 11 | 300 | 150 | 20 |
| Comparative Example 1 | 20 | 130 | 30 |
| Comparative Example 2 | 50 | 130 | 30 |
| Comparative Example 3 | 580 | 130 | 10 |
| Comparative Example 4 | 1100 | 130 | 10 |

[a](glycerol weight * 100)/(carboxymethylcellulose + glycerol) weight

Example 12. Preparation of the Surgical Mesh Composite

A. Preparation of Surgical Mesh

In accordance with the method disclosed in Korean patent No. 10-0946338, the segmented-pie type monofilament was prepared by conjugate spinning at 4:6 of a volumetric ratio of polypropylene and polycaprolactone, and the mesh was prepared by using the segmented-pie type monofilament as a warp knit.

B. Preparation of Biodegradable Polymer Adhesive Layer

The copolymer with a weight-average molecular weight of 70,000 D prepared from glycolide and lactide at a mixing weight ratio of 3:7 was dissolved in methylene chloride to a concentration of 5 wt %. The obtained solution was cast on the glass petri dish to produce a film of poly(glycolide-co-lactide) with a 120 mm of diameter and 0.35 mm of thickness.

C. Preparation of Mesh Composite

The poly(glycolide-co-lactide) film obtained in B section was positioned between the anti-adhesion layer obtained in Examples 1 to 11 and the mesh, and then adhered on the hot plate at 120° C. by applying 10 psi for 60 seconds. After removing the pressure and cooling slowly, the three-layered mesh composite including the mesh and the anti-adhesion layer adhered by the poly(glycolide-co-lactide).

The three-layered mesh composite is shown in FIG. 1 and includes a surgical mesh later, a biodegradable polymer adhesive layer and an anti-adhesion layer. The thickness of the mesh composite is 850 μm, the thickness of mesh layer is 500 μm, the thickness of the adhesive layer is 50 μm, and the thickness of the anti-adhesion layer is 300 μm.

Example 13. Test of the Property of Mesh Composite

To test the anti-adhesion effect of the surgical mesh composite obtained in Example 12, the test animal was SD rat (Orient bio Ltd.). 10 or more male rat aged 6 weeks or longer were used and raised individually at 16 to 22° C. and at a relative humidity of 50 to 70%.

The abdomen of rat under anesthetic was cut to induce the artificial hernia, and the intestine touched to the hernia region was hurt to take off the surface. Then, the size 3*2 cm section of surgical mesh composite was put over the abdominal wall and sutured the incised region. 1 week after the operation, the maintenance of the artificial hernia was checked and the degree of adhesion in the tissue was evaluated by measuring the region area of the mesh not adhereing to the organ and serosa(?) and calculating the mean value of ratio to the total area of the mesh composite.

The degrees of the anti-adhesion effects were obtained as being dependent on 1) the viscosity of carboxymethylcellulose solution used for preparing the insoluble carboxymethylcellulose, 2) the content of glycerol in the anti-adhesion layer and 3) the temperature of heat treatment for preparing the insoluble anti-adhesion layer. The results were shown in Tables 2 to 4. As a control group, the mesh of Example 12. A without including the anti-adhesion layer was inserted into the abdomen and sutured.

TABLE 2

The effect of different viscosity of carboxymethylcellulosesolution

| mesh composite | Anti-adhesion rate [%] |
|---|---|
| Example 1 | 60 |
| Example 5 | 85 |
| Comparative Example 2 | 32 |
| Comparative Example 3 | 17 |
| Control | 13 |

As shown in Table 2, the control that the mesh of Example 12. A without including the anti-adhesion layer was used, showed 13% of non-adhering area with respect to the total mesh area, which is a very low anti-adhesion effect. In the comparative Example 3 that the viscosity of carboxymethylcellulose solution was 580 cps in spite of inclusion of the anti-adhesion layer, the anti-adhesion rate was 17%, which was not much higher anti-adhesion effect compared to that of control group. In Comparative Example 2 that the viscosity of carboxymethylcellulose solution was 50 cps in spite of inclusion of the anti-adhesion layer, the mesh composite showed a low anti-adhesion rate of 32%.

On the other hand, the mesh composites including the anti-adhesion layers in the Examples 1 and 5 where the viscosities of carboxymethylcellulose solution were 110 cps and 300 cps respectively showed the anti-adhesion rates of 60% and 85% respectively, thereby providing the remarkable anti-adhesion effect. Thus, when the viscosity of carboxymethylcellulose solution was excessively low or high as Comparative Examples 2 and 3, the significant anti-adhesion effect could not be obtained. The anti-adhesion layer prepared according to the Examples of the present invention using carboxymethylcellulose solution with the suitable viscosity ranges, especially Example 5 of viscosity 300 cps showed very high anti-adhesion effect.

TABLE 3

The effect of glycerol content

| mesh composite | anti-adhesion rate[%] |
|---|---|
| Example 3 | 55 |
| Example 4 | 80 |
| Example 5 | 85 |
| Control | 13 |

To test the effect of the addition of glyceol to the anti-adhesion layer on the anti-adhesion effect, the viscosity of carboxymethylcellulose solution and the conditions of heat treatment were set to be equal conditions (300 cps, 130° C.), the content of glycerol was adjusted to be 0 wt % (Example 3), 10 wt % (Example 4), and 30 wt % (Example 5) and experimented for the anti-adhesion effect. The results were shown in Table 3, Example 3 without including glycerol showed the significant anti-adhesion effect (55%), but the addition of glycerol showed higher anti-adhesion effect. In particular, Example 5 including 30 wt % of glycerol showed 85% of anti-adhesion effect.

TABLE 4

Effect of the temperature of heat treatment

| mesh composite | anti-adhesion rate[%] |
|---|---|
| Example 8 | 50 |
| Example 9 | 70 |
| Example 10 | 70 |
| Example 11 | 60 |
| Control | 13 |

To test the effect of temperature of heat treatment for preparing the insoluble carboxymethylcellulose on the anti-adhesion property, the viscosity of carboxymethylcellulose solution and the content of glycerol were set to be equal conditions (300 cps, 20 wt %), the temperature of heat treatment was adjusted to be 100° C. (Example 8), 120° C. (Example 9), 140° C. (Example 10) and 150° C. (Example 11). As shown in Table 4, Examples 8 to 11 showed 50% or higher anti-adhesion rate. As the temperature of heat treatment increases, the anti-adhesion effect becomes higher. However, in case that the anti-adhesion layer used the insoluble carboxymethylcellulose prepared by the heat treatment at 150° C., the anti-adhesion effect was reduced rather, compared to the anti-adhesion layer using the insoluble carboxymethylcellulose prepared by the heat treatment at 140° C. In the case that the anti-adhesion layers used the insoluble carboxymethylcellulose prepared by performing the heat treatment at 120° C. and 140° C. respectively, they showed highest anti-adhesion rate of 70% (see Examples 9 and 10).

What is claimed is:

1. A surgical mesh composite, comprising a surgical mesh layer and an anti-adhesion layer and having an anti-adhesion property, wherein the anti-adhesion layer consists of a mixture of insoluble carboxymethylcellulose and polyhydric alcohol.

2. The surgical mesh composite according to claim 1, wherein the carboxymethylcellulose is an alkali salt of carboxymethylcellulose.

3. The surgical mesh composite according to claim 1, wherein the polyhydric alcohol is present at an amount of 100 parts by weight or less, with respect to 100 parts by weight of carboxymethylcellulose.

4. The surgical mesh composite according to claim 1, wherein the polyhydric alcohol is glycerol.

5. The surgical mesh composite according to claim 1, wherein the anti-adhesion layer is contained at 10 to 90 parts by weight, with respect to 100 parts by weight of the surgical mesh composite.

6. The surgical mesh composite according to claim 1, wherein the thickness of surgical mesh composite ranges from 100 to 900 μm.

7. The surgical mesh composite according to claim 1, which further comprises a biodegradable polymer adhesive layer located between the surgical mesh layer and the anti-adhesion layer.

8. The surgical mesh composite according to claim 7, wherein the biodegradable polymer adhesive layer is contained at 0.1 to 60 parts by weight, with respect to 100 parts by weight of the surgical mesh composite.

9. The surgical mesh composite according to claim 8, wherein the biodegradable polymer has a weight-average molecular weight of 10,000 to 200,000 D.

10. The surgical mesh composite according to claim 7, wherein the biodegradable polymer is a homopolymer or a copolymer prepared from at least one monomer selected from the group consisting of glycolide, glycolic acid, lactide, lactic acid, ε-caprolactone, ρ-dioxanone, trimethylene carbonate, polyanhydride and polyhydroxyalkanoate.

11. A method of preparing a surgical mesh composite according to claim 1, comprising providing a surgical mesh layer; preparing an anti-adhesion layer consisting of a mixture of insoluble carboxymethylcellulose and polyhydric alcohol, wherein the insoluble carboxymethylcellulose is formed by heat treatment of carboxymethylcellulose with a viscosity of 100 cps to 500 cps in 1 wt % of solution; and adhering the anti-adhesion layer on the surgical mesh layer.

12. The method according to claim 11, wherein the adhering step is performed by placing a biodegradable polymer adhesive layer located between the surgical mesh layer and the anti-adhesion layer, and performing a heat-sealing.

13. The method according to claim 12, wherein the heat-sealing is performed with a plate heated at a temperature of 50 to 200° C. under a pressure of 10 to 1,500 psi.

14. The method according to claim 11, wherein the heat treatment is performed at a temperature of 100 to 160° C.

15. The method according to claim 11, wherein the heat treatment is performed at a pressure of 2,000 mmHg or lower.

16. The method according to claim 11, wherein the mixture of carboxymethylcellulose and polyhydric alcohol is a product obtained by freezing and drying the mixture of carboxymethylcellulose and polyhydric alcohol.

* * * * *